United States Patent [19]
Stockham et al.

[11] Patent Number: 5,273,632
[45] Date of Patent: Dec. 28, 1993

[54] METHODS AND APPARATUS FOR ANALYSIS OF CHROMATOGRAPHIC MIGRATION PATTERNS

[75] Inventors: Thomas G. Stockham; Jeffrey T. Ives, both of Salt Lake City, Utah

[73] Assignee: University of Utah Research Foundation, Salt Lake City, Utah

[21] Appl. No.: 978,915

[22] Filed: Nov. 19, 1992

[51] Int. Cl.[5] ............... B01D 57/02; B01D 15/08
[52] U.S. Cl. ................... 204/180.1; 364/497; 210/656; 935/77; 935/85; 935/86; 935/87; 204/182.8
[58] Field of Search ............ 204/299 R, 182.8, 180.1; 364/497; 210/656; 935/77, 85, 86, 87

[56] References Cited

U.S. PATENT DOCUMENTS

| | | | |
|---|---|---|---|
| 4,720,786 | 1/1988 | Hara | 364/413 |
| 4,837,726 | 6/1989 | Hunkapiller | 364/498 |
| 4,868,749 | 9/1989 | Kimura et al. | 364/413.13 |
| 4,885,696 | 12/1989 | Hara | 364/497 |
| 4,941,092 | 7/1990 | Hara et al. | 364/413.15 |
| 4,958,281 | 9/1990 | Hara | 364/413.01 |
| 4,980,827 | 12/1990 | Hara | 364/413.01 |

OTHER PUBLICATIONS

T. Stockham, Jr. et al., "Blind Deconvolution Through Digital Signal Processing," Proceedings. of the IEEE, vol. 63, No. 4, Apr. 1975.

*Primary Examiner*—John Niebling
*Assistant Examiner*—C. Delacroix-Muirheid
*Attorney, Agent, or Firm*—Trask, Britt & Rossa

[57] ABSTRACT

A method and apparatus for sharpening signal peaks in a signal representing the distribution of biological or chemical components of a mixture separated by a chromatographic technique such as, but not limited to, electrophoresis. A key step in the method is the use of a blind deconvolution technique, presently embodied as homomorphic filtering, to reduce the contribution of a blurring function to the signal encoding the peaks of the distribution. The invention further includes steps and apparatus directed to determination of a nucleotide sequence from a set of four such signals representing DNA sequence data derived by electrophoretic means.

33 Claims, 9 Drawing Sheets

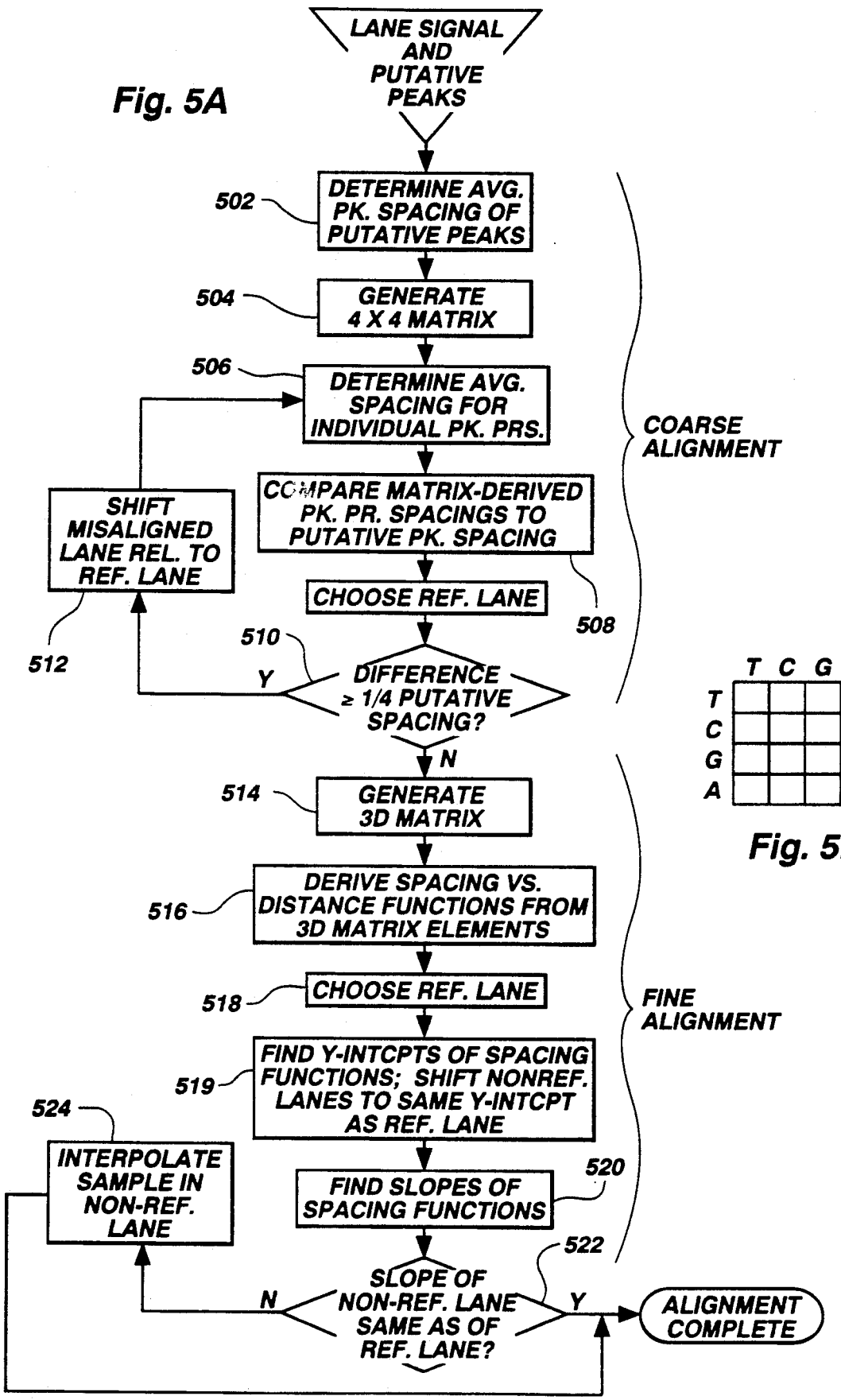

METHODS AND APPARATUS FOR ANALYSIS OF CHROMATOGRAPHIC MIGRATION PATTERNS

This invention was made with Government support under grant number DEFG0288ER60700 awarded by the Department of Energy. The government has certain rights in the invention subject to the provisions of 37 C.F.R. § 401 and 45 C.F.R. §8.

BACKGROUND OF THE INVENTION

1. Field:

This invention relates generally to signal processing analysis of chromatographic migration patterns such as are commonly used in chemistry and in biology to analyze mixtures of molecules, and further to such analysis applied to the determination of DNA sequences.

2. State of The Art:

Electrophoretic migration patterns may be visualized by a number of different techniques. However, most of these techniques depend upon an electromagnetic radiation-emitting tag attached to the molecule(s) of interest. Such a tag may be a radioactive isotope emitting X-ray photons, beta particles, alpha particles, etc, a fluorescent tag emitting photons of UV, visible or infrared light, or the like. The emissions of these tags are generally detected by photographic films or by a detector sensitive to the emission, and converted into a visual image indicating the amount of label migrating in different regions of the electrophoretic medium. The electrophoretic medium is often a porous gel medium on which a film may be overlaid or which may be scanned by a detector. More recently, methods for performing electrophoresis in a liquid medium have been developed; here the tag is usually detected as the molecule carrying it passes adjacent to a fixed detector.

Whatever the method of visualization, the resulting image depicts the amounts of tagged molecules migrating at different linear positions in the electrophoretic medium. The methods described in this application are suitable for analysis of migration patterns obtained by any of the foregoing means.

At present, the analysis of DNA sequences of large DNA segments is particularly important in connection with the Human Genome Project, as well as for many other research and industrial purposes Biochemical methods for sequencing DNA are well-known, which involve electrophoresing four replicate sets of DNA fragments generated from the DNA molecule being sequenced. Each set contains a series of labelled fragments varying in length and terminating in a single respective one of the four standard DNA nucleotides A (adenine), T (thymine), G (guanine) and C (cytosine) That is, all of the tagged fragments in one sample terminate in A residues, in another sample all fragments terminate in T residues, etc. The samples are electrophoresed in one dimension and the migration patterns visualized by one of the methods mentioned hereinabove. The result is a pattern of four lanes in which each lane has a series of bands corresponding to the positions of fragments terminating in a particular one of the four bases adenine, thymine, guanine and cytosine.

The biochemical portions of these methods have been automated and thus greatly speeded up. However, a serious bottleneck remains in the determination of the sequence from the set of four ladders. Most often, a skilled individual reads the sequence by aligning the lanes of the four samples and making judgements as to what band images represent "true" bands representing a tagged fragment, and which are due to noise or overlapping of small features resulting from noise or variations in the biochemical portion of the assay. This process is tedious, time-consuming, and not as accurate as is desired: a skilled human reader requires at least 2 hours to analyze a film containing sequences totalling about 5000 nucleotides. For comparison, the human genome is estimated to require reading of an absolute minimum of about one to two million films, or two to four million man-hours. The error rate even by skilled readers is generally above 1%, which is unacceptably high.

It is highly desirable to analyze the patterns automatically by computer. The visualized patterns can readily be digitized to provide a signal that can be analyzed by signal processing technology and/or computer. However, there are several problems which complicate the analysis. First, the spacing of bands produced by fragments differing in length by a single nucleotide tends to change with size of the fragment. There may also be differences in the spacing of bands among the four lanes. Additionally, since detection of these bands is essentially detection of the label by means of electromagnetic radiation, there is a spread or dispersion due to the stochastic nature of the electromagnetic radiation emissions. There is background noise resulting from both factors in the biochemical technique and in the detection of electromagnetic radiation, which results in a generally low but variable pattern of visual darkening or visual signal over the lane. The general intensity of labelling often varies between the four lanes, and there is furthermore a tendency for bands within a given lane to vary in relative intensity in an unpredictable manner.

All of above factors serve to confuse the identification of individual peaks and the correct ordering of the peaks, leading to errors in the determined sequence. Furthermore, all of these factors vary from one quartet of ladders to the next, so that it is not possible to determine a blurring "noise characterization" which may be applied to any quartet of visualized band patterns. Instead, the visual images are commonly interpreted by a skilled human reader.

To compensate for the differing distances between fragments which differ by one base in length, commonly the reader makes some comparative measurement of the spacing between fragments at two or more points in the vertical length of the lane and then enters this into the computer. Similarly, the background level in different regions of each lane of a quartet must be determined and entered into the computer. These values apply only to the single image being analyzed at that time. The parameters may not be useful to analyze a different image. Thus, there is a great deal of operator input and tedious work required simply to set up the visual image for the computerized analysis, slowing the process.

Therefore, a need remains for a method of computerized analysis of the visual images of DNA sequence ladders which does not require the inputting or determination of specific parameters for each individual autoradiograph by an operator and which can rapidly and accurately produce sequences for a number of different autoradiographs. Furthermore, because the amount of data to be analyzed for any one sequence is substantial, for example, may consist of several thousand bases, it is desirable to have such a method which will utilize or conform to the methods of most rapid signal processing, thus reducing the amount of computer time required for the analysis and save both time and money.

Definitions

For purposes of this application, certain terms are defined as follows:

"Sample" refers to a point having a signal value which represents one of a series of measurements made at selected intervals; for example, the signal value corresponding to a point at which a digitizing scanner measures the optical density of an exposed film such as an autoradiograph.

"Log-spectrum" denotes the complex logarithm of a Fourier transform of the scan signal. It contains a real portion and an imaginary portion.

"Cepstrum" refers to a function obtained by subjecting a log-spectrum to an inverse Fourier transformation.

"Lifter" refers to a filter function designed to operate in a second or cepstral domain, that is, in the domain in which the cepstrum exists. Similarly, "liftering" is analogous to filtering, except that it takes place in the second space domain.

"Quefrency" denotes the abscissa in the domain in which the cepstrum and the lifter exist.

BRIEF DESCRIPTION OF THE DRAWINGS

In the drawings which depict what is currently regarded as the best mode for carrying out the invention.

FIG. 5A is a flow chart depicting the alignment process of step 214 in FIG. 2 in greater detail;

FIG. 5B depicts a 4×4 matrix used in the alignment process of FIG. 5A;

SUMMARY OF THE INVENTION

Figure 1:
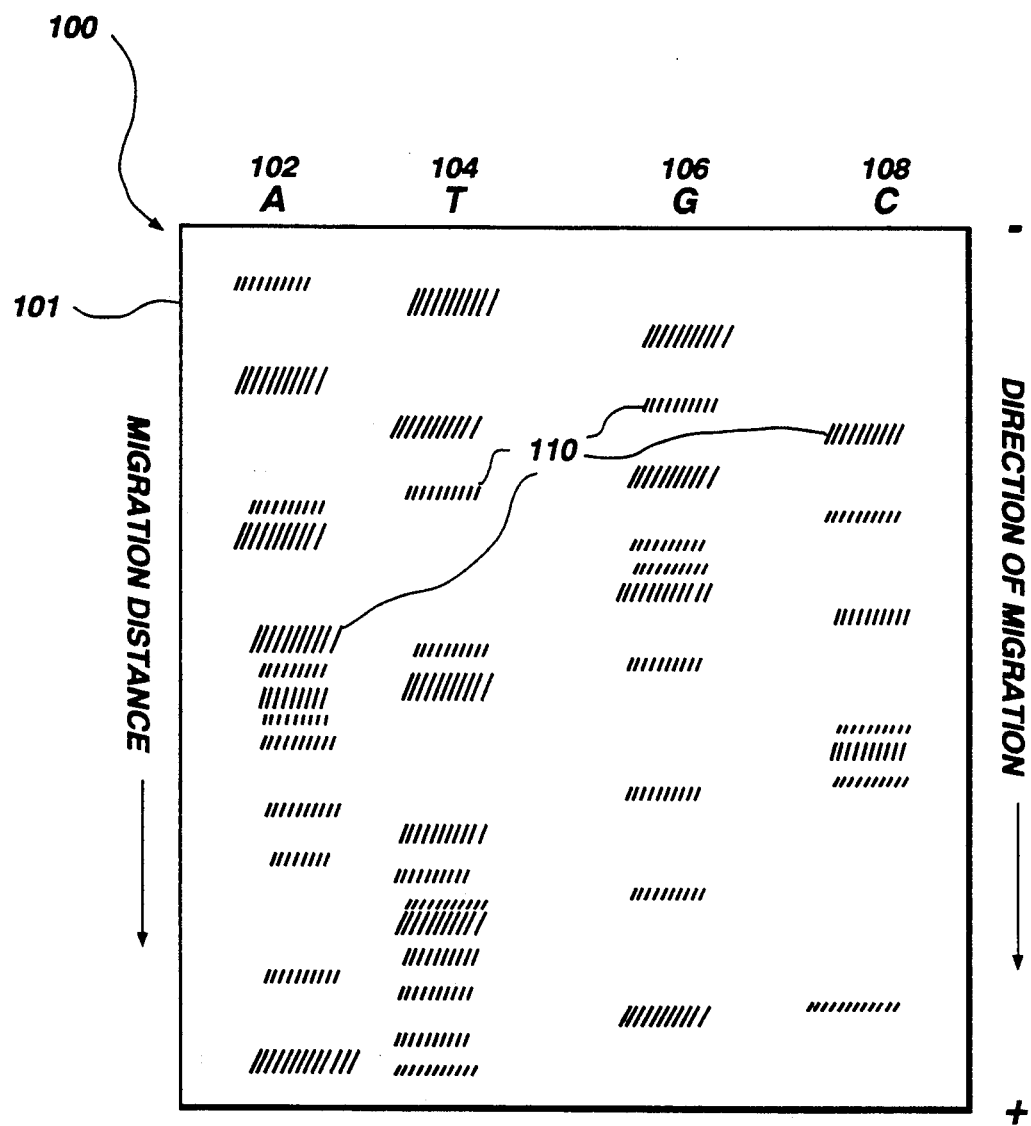
FIG. 1 depicts a typical autoradiogram of a DNA sequencing gel.

The invention comprises a method and an apparatus for sharpening signal peaks in a signal representing the distribution of biological or chemical components of a mixture separated by a chromatographic technique such as, but not limited to, electrophoresis. The invention further includes steps and apparatus directed to determination of the nucleotide sequence from a set of four such signals representing DNA sequence data derived by electrophoretic means. Such sequence data take the form of a quartet of lanes each having a ladder-like pattern of bands. The band pattern in each lane corresponds to the migration pattern of fragments labeled with a respective one of the four major nucleotides found in DNA.

A key step in the method is the use of blind deconvolution to sharpen the peaks in a lane signal which represents the relative amount of a selected component versus migration distance for a given lane. By "blind" deconvolution, it is meant that the blurring function need not be precisely known to perform the deconvolution, nor is there any need for a noise reading or other information from the individual chromatogram being analyzed. Once the parameters of the blind deconvolution are defined for a particular chromatographic technique, no further information concerning background noise or other interfering signals is needed to process additional chromatograms made by that technique. In the presently preferred embodiment, homomorphic filtering is the procedure employed for blind deconvolution.

The presently preferred embodiment includes the following steps. First, a lane signal which represents the amount of label versus migration distance for a particular lane is provided. If the lane signal is based on a logarithmic or other non-linear scale, it is converted to a linearly-scaled lane signal. Next, the linearized lane signal is transformed from the first space domain to a cepstral domain, where it is subjected to linear filtering with a lifter function (a filter applied in a cepstral domain) selected to separate the desired signal from most or all of a blurring function. The linear-filtered signal is then de-transformed back to the original space domain, and at the same time subjected to further filtering to remove background noise.

The transformation to the cepstral domain involves three steps. First, the digital lane signal, which is in a first space domain, is converted by Fourier transformation to a frequency spectrum signal (FS signal) in a frequency domain. Next, the complex logarithm of the FS signal is taken, producing a complex log-spectrum (CLS) signal having a real and an imaginary portion. Finally, the real portion of the CLS signal is subjected to an inverse Fourier transform to produce a cepstrum signal in a second space domain.

After the cepstrum signal is manipulated by a liftering function in the second space domain, it is detransformed back to the original (first) space domain. This de-transformation is accomplished by performing a Fourier transform on the liftered cepstral signal to get the liftered log-spectrum (LLS) filtered signal, taking the antilog of the LLS filtered signal to produce the liftered frequency spectrum (LFS) signal, and performing an inverse Fourier transform to regenerate a deconvolved lane signal in the original space domain.

Optionally but highly desirably, a low-pass filter is inserted in the de-transformation sequence to reduce background noise.

The lifter, also referred to herein as the linear filtering function, is chosen and adjusted to remove most of the effects of the blurring function Additionally, the lifter effectively adjusts the amplitude range of the cepstrum lane signal to a selected standard scale. A significant advantage of the latter feature is that, when all the lane signals from a set of four lanes of a DNA sequencing reaction have been deconvolved using the same lifter function, the signals have also been normalized to each other. The normalization of all the signals in the quartet greatly facilitates the subsequent steps in which multiple lane signals in a set are mutually processed to produce a DNA sequence.

The foregoing steps of homomorphic filtering and deconvolution may be used to sharpen "true" peaks of any spectral-type signal representing the relative spatial distribution of biological or chemical constituents or molecular components in a mixture subjected to separation by chromatography or like methods, including but not limited to: electrophoresis, affinity chromatography, high-pressure liquid chromatography, flow cytometry of cells and subcellular components, and the like. The lifter function and the use of a noise filter may be varied to accommodate the needs of different separation technologies.

To derive a DNA sequence from a set of four lane signals, the foregoing steps of linearization, blind deconvolution, and noise filtering are performed on each of the four lane signals. The result is a set of four deconvolved lane signals, one for each of the four standard nucleotides.

Next, a group of provisional "true" peaks are identified in each lane signal Peak identification is performed by selecting peaks whose intensity exceeds a chosen threshold intensity In a preferred embodiment, within a given lane the threshold level is varied with migration distance so as to substantially match the actual variation in peak height within that lane.

An alignment or cross-registering procedure is then applied to the quartet of deconvolved signals to determine the order and spacing of peaks among the four lanes. In the illustrated working embodiment, the peak spacing is adjusted as necessary according to a protocol in which a 4×4 matrix of lane-lane interpeak distances is generated, and the lanes are shifted relative to one another until satisfactory values of interpeak distances are achieved. In the preferred embodiment of the alignment procedure, the four lane signals are aligned not only to give a proper order of peaks, but also to have the peaks substantially centered within the interpeak intervals.

Once a satisfactory alignment is achieved, the provisional peak selections are further refined on the basis of interpeak spacing considerations, to fill in "missing" peaks and/or eliminate spurious peaks.

Finally, after the refinement of the peak selection is complete, the putative DNA sequence of the starting DNA molecule is read off ("base-called") from the order of the selected signal peaks and the identity of their respective lanes.

The invention includes an apparatus which is constructed to perform the method.

DETAILED DESCRIPTION OF THE ILLUSTRATED EMBODIMENTS

FIG. 1 depicts an autoradiogram made by exposing a photographic film to a gel of a set of four DNA sequencing samples. The autoradiogram 100 has four lanes 102, 104, 106, 108, which correspond respectively to sequencing samples A (adenine), T (thymine), G (guanine), and C (cytosine). Each of lanes 102, 104, 106, 108 has a series of bands 110 which are produced by the label at the end of each series of fragments labeled with the corresponding base (A, T, G, C). Autoradiogram 100 is a visual representation typical of that obtained with gel electrophoresis of radioactively labelled fragments, which is one widely used method for determining the relative electrophoretic migration distances of fragments in DNA sequencing samples.

Figure 6:
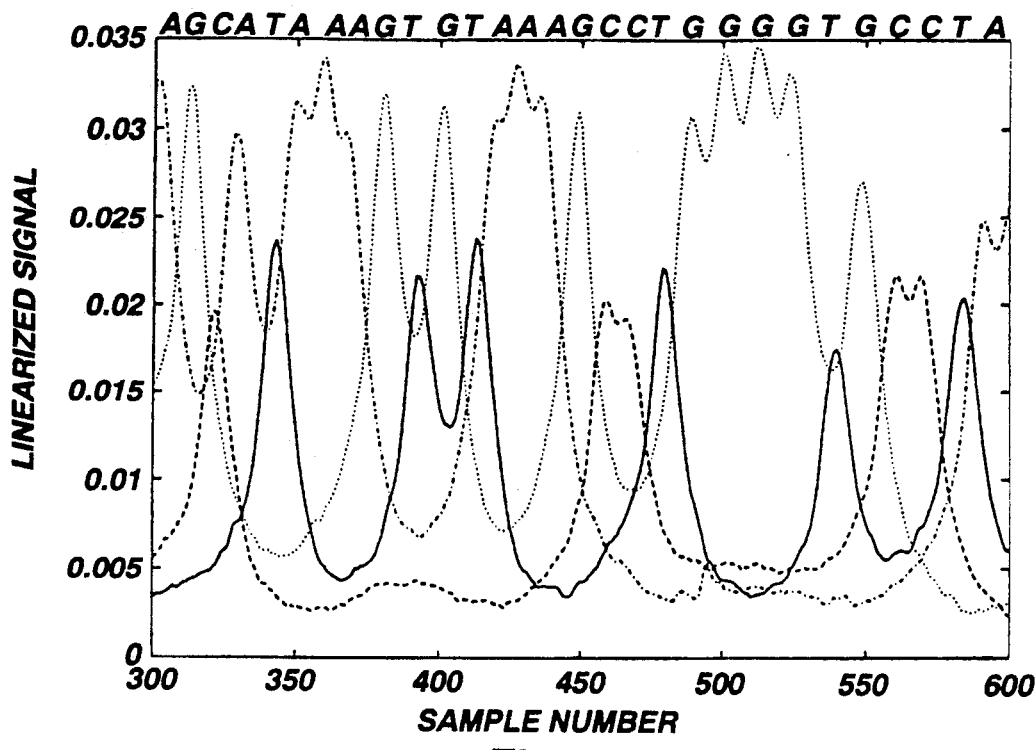
FIG. 6 depicts a set of four linearized lane signals obtained from an autoradiogram similar to that of FIG. 1.

FIG. 6 depicts a group of four lane signals obtained by scanning an autoradiogram such as that shown in FIG. 1 with a digitizing scanner. Each of the digital lane signals 602, 604, 606, 608 comprises a series of samples whose values represent the relative amount of label as a function of migration distance. Bands such as bands 110 in FIG. 1, are represented in these signals as peaks of high signal intensity. Lane signals 602, 604, 606 and 608 correspond respectively to the detection of label from fragments terminating in A (adenine), T (thymine), G (guanine), and C (cytosine) nucleotides.

When the labelled nucleotides are visualized by autoradiography, to attain good results with the invention certain conditions should be met. First, the film should have a dynamic range of at least about two optical density units (abbreviated O.D.), and the dynamic range of the scanner should meet or exceed the range between the background and the darkest bands. Additionally, whether a film or other detector is used, care should be taken to assure that the film or detector range is not saturated, while at the same time providing adequate detection of low-intensity bands. Third, the film scanner or other lane signal-producing detector should take samples at an interval which meets the criterion of the well-known Nyquist sampling theorem. In the working embodiment applied to autoradiographs, it is found that sampling at intervals of about 150 to 100 microns or less is sufficient to attain good results.

If the lane signal is based on a logarithmic or other nonlinear intensity scale, as is commonly true for signals produced by film scanners, for purposes of the working embodiment employing homomorphic filtering it is highly desirable that the lane signal be linearized. FIG. 6 depicts lane signals which have been linearized.

Figure 2:
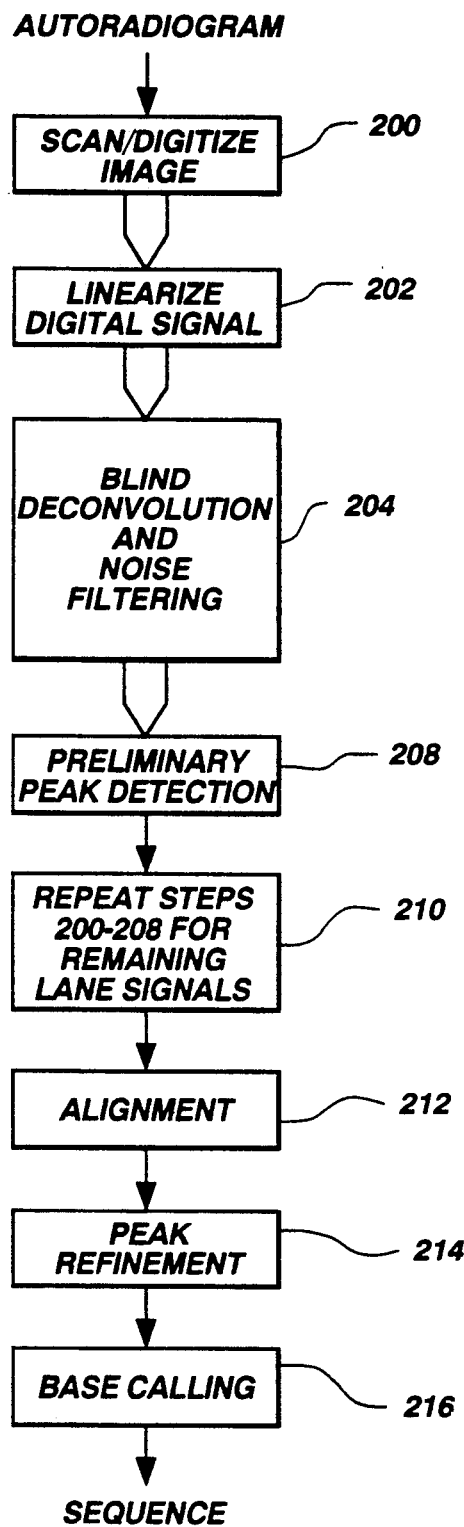
FIG. 2 is a flow chart of steps representing the steps in a method for computerized analysis of DNA sequence ladders.
Figure 3:
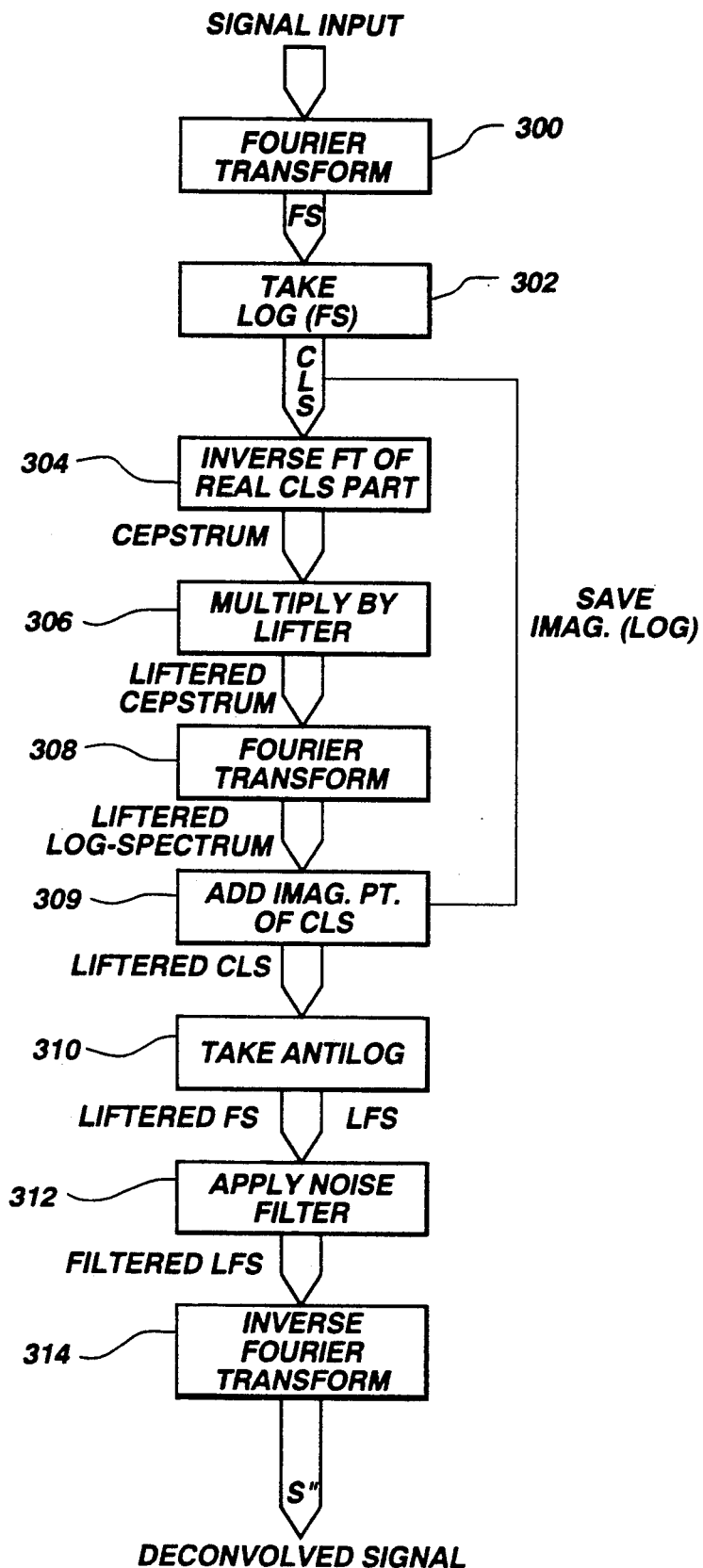
FIG. 3 is a flow chart showing details of a method of performing the blind deconvolution step 204 of FIG. 1, employing homomorphic filtering.

Additionally, in the working embodiment of the method described in reference to FIGS. 2 and 3, the lane signals are processed in digital form. That is, either the film scanner should produce the lane signals as digitized lane signals, or if the scanner produces analog signals these should be converted to digital lane signals before the peak sharpening process is applied. The lane signals depicted in FIG. 6 are 300-sample segments of digital lane signals.

A method of using blind deconvolution to sharpen peaks in an individual lane signal by reducing the contribution of a blurring function, is depicted in the flow chart of FIG. 3. For purposes of description, the blind deconvolution method will be described primarily with reference to lane signals obtained by scanning an autoradiograph like that of FIG. 1.

In the illustrated embodiment, the blind deconvolution employs homomorphic filtering (FIG. 3). The linearized lane signal is considered to be a convolution of two or more separate signal functions, the desired signal function and a blurring function, with an additional contribution of random background noise. The blurring function is believed to include the effects of the natural spatial dispersion of electromagnetic radiation from a point source, plus the well-known phenomenon of variation in exact migration distance in the electrophoretic medium observed for fragments of the same length. The result of the noted effects is blurring and overlapping of bands or peaks in the signal which interferes with identification of true peaks and with the assignment of correct relative positions of peaks in different lane signals.

Referring to FIG. 3, a lane signal, whose signal intensity increases essentially linearly with the amount of label detected, is subjected to a Fourier transform (step 300), resulting in a frequency spectrum (FS) signal. Next, the complex logarithm of the FS signal is taken (step 302), thus producing a complex log-spectrum signal (CLS signal); the CLS signal has a real and an imaginary portion.

The real portion of the CLS signal is then subjected to a first inverse Fourier transformation (step 304), which transforms it into a second space domain. The inverse Fourier transform of the CLS signal is termed a cepstrum or cepstral signal. The cepstrum is then multiplied by a lifter function which reduces or removes the blurring function.

From a plot of the cepstrum (FIGS. 8, 9), it can be seen that the region in which the blurring signal(s) predominate is in the low-frequency range. Accordingly, the lifter function is chosen to have a wavenumber response of a high-pass type. That is, the amplitudes of the cepstrum signal at small wavenumbers (small frequencies) are substantially attenuated or set to zero. Further desirably, the shape of the lifter function should be as nearly the inverse of the shape of the portion of the cepstrum in which the blurring signal(s) predominate. In the presently preferred embodiment, the lifter function has a 50% raised cosine taper which starts at a selected point (for example, at arrow 910 in FIG. 9) which is near the point that the cepstrum levels off.

Other lifter designs are possible, including lifter functions designed to satisfy a desirable error criterion (for example Weiner filtering). However, at the present it is believed that such other designs would not achieve significantly better results than the design disclosed herein. In the illustrated embodiment, the results obtained are consistent with the assumption that the portion of the blurring function which is expected to be due to electromagnetic emission scatter has the approximate form of a Lorentzian equation. However, other models of radiation scatter may be useful, depending on the nature of the detection system and the type of electromagnetic radiation emitted by the label (e.g. particle or photon type and energy). The degree of spreading of a band due to slight variations in the migration distance of fragments which are of essentially the same length is unknown. In any case, for analysis of autoradiograms, satisfactory results are achieved if both the radiation scatter and migration blurring effects are assumed to appear as a low-frequency component in the second space domain, and the lifter is chosen to eliminate that component while preserving the desired signal components.

Multiplication of the cepstrum by the lifter function (step 306) substantially reduces blurring due to the blurring function and sharpens the "true" peaks. Thus, step 306 removes most of the signal portion produced by the blurring function from the desired signal which represents the distribution of DNA fragments, producing a liftered cepstrum signal.

The liftered cepstrum signal produced from step 306 is now de-transformed back to the first space domain. A second Fourier transformation is performed (step 308), which converts the liftered cepstrum signal to a liftered log-spectrum signal (LLS signal) in the frequency domain. At this point, the imaginary part of the CLS signal is added back to the LLS signal to produce a liftered CLS signal. The inverse logarithm of the liftered CLS signal is then taken (step 310), resulting in a liftered frequency spectrum signal (LFS signal).

Figure 12:
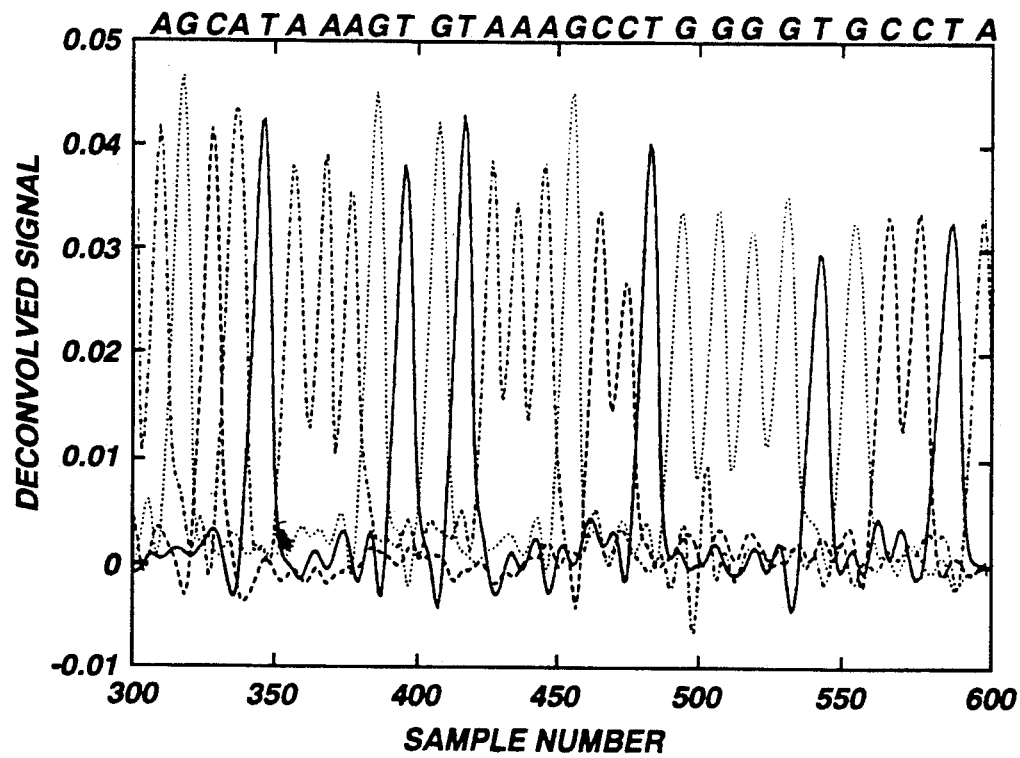
FIG. 12 depicts a set of deconvolved lane signals produced by subjecting the linearized lane signals of FIG. 6 to the complete method of FIG. 3.

Optionally but highly preferably, the LFS signal is then filtered with a low-pass filter which removes high frequencies to a degree such that the resulting signal peaks in the deconvolved signal (FIG. 12 after step 314) do not overlap but are also without significant gaps between adjacent peaks. A result such as that shown in FIG. 12 is believed to be near optimal (step 312). A low pass filter useful to obtain such a result is a Gaussian filter having a bandpass width of between about 50 and about 150 frequency samples when $\pi$ is 1024 samples. For a signal wherein $\pi$ corresponds to a different number of samples, a useful bandpass width may be computed relative to the above values. The frequencies above the cut-off are believed to correspond primarily to background noise resulting from the detection methods which can be used with electromagnetic radiation-emitting labels. The result of step 312 is a filtered LFS signal.

Finally, the filtered LFS signal subjected to an inverse Fourier transformation (step 314), producing a deconvolved lane signal in the original space domain. Since the imaginary part of the CLS signal was not changed, the phase of the deconvolved lane signal is also unchanged from that of the original lane signal.

In addition to the homomorphic filtering, it has been found that noise filtering is generally required to produce satisfactory results. In the embodiment of FIG. 3, step 312 applying a low-pass filter to the LFS signal is included specifically for that purpose. Alternatively, the noise may be reduced by truncating the FS (frequency spectrum) signal or the CLS (complex log-spectrum) signal at or above the frequency at which the noise dominates. The signal so treated is then subjected to the remaining steps 304 to 314 as described, except that step 312 is now omitted. This alternate method is theoretically superior, but at present is difficult and costly to implement, and the improvement which may be achieved is not at this time believed to be sufficient to justify the disadvantages.

Still another alternative is to apply a noise filter substantially equivalent to that of step 312, to the deconvolved signal instead of the LFS signal and the results will be virtually identical to those of the preferred embodiment. However, this is far less efficient in terms of processing time. The presently preferred embodiment for noise filtering is that depicted in FIG. 3.

A significant advantage of the use of homomorphic filtering for blind deconvolution, is that the lifter function of step 306 normalizes the cepstrum to a fixed and selectable intensity range. Thus, when each of the four signals of the set have been processed by this homomorphic filtering, they have all been normalized to the same standard and therefore to each other. This normalization greatly facilitates subsequent analysis; for example, in the case of a DNA sequence, the steps of preliminary peak detection, alignment, and peak refinement.

Furthermore, once a lifter function and noise function have been established for a given chromatographic technique (which is here understood to mean not only the chromatographic separation but also to include the method by which the separated components are visualized), additional chromatograms obtained with that technique can be processed with the same functions with very good results.

Although the method has been described in terms of digitized signals, it is equally feasible to perform the method upon analog lane signals.

Homomorphic filtering has also been applied to signal analysis of signals derived from photographic images, tape recordings, and the like. (Reference: *Digital Signal Processing*, A.V. Oppenheim and R. Schafer, authors, Prentice-Hall (1975) Chapter 10. An important aspect of the homomorphic filtering as applied in the present method is the insertion of a noise filter between step 310 and step 314. A significant advantage of homomorphic filtering in the present invention is that it is extremely compatible with modern high-speed signal processing methods, thus speeding the analytic process, reducing the amount of computer time required, and the necessary computing capacity of a computer performing the method. The expense of the method is therefore considerably reduced.

FIG. 2 depicts a method of determining a DNA sequence from a set of four lane signals such as lane signals 602, 604, 606, 608 depicted in FIG. 6, or lane signals describing an electrophoretic migration pattern of a DNA sequencing reaction obtained by other means.

First, a linearized lane signal is provided from a film scanner or other detection means. To sharpen the peaks by reducing the contribution of the blurring function, the linearized lane signal is subjected to blind deconvolution (step 204), producing a deconvolved signal. A method for performing blind deconvolution is described previously herein with reference to FIG. 3.

Optionally and highly preferably, a step of filtering 206 is performed following and/or in conjunction with the blind deconvolution, to reduce or remove background noise. Again, in a highly preferred embodiment the filtering of background noise does not require use of a background noise signal obtained from a blank region of the autoradiograph or other image being analyzed. Filtering step 206 is discussed in greater detail as it pertains to homomorphic filtering, with reference to FIG. 3.

A deconvolved signal resulting from steps 204, 206 is then subjected to a preliminary peak detection step 208. In step 208, a group of putative peaks is established by selecting all peaks which exceed a preset threshold intensity. Preferably, the threshold intensity varies with migration distance, that is, with position in the signal. The putative peaks includes all peaks whose height (intensity) exceeds the value of the threshold function at their position.

In the presently preferred embodiment, the threshold function is established by the following steps. First, the lane is divided into a series of segments each spanning between about 20 to 40 sequential bands or peaks. Within each segment, an average peak height is computed for a selected small group of the largest and/or most clearly resolved peaks. The peaks from which this average peak height is computed, are individually identified as a sample having a high value with samples of lower intensity values immediately adjacent on both sides. A group size of about four peaks per segment has been found to give satisfactory results. For each segment, a tentative threshold value is determined as a selected fraction of the average peak height for that segment; the same proportionality is used for all the segments. Generally, a tentative threshold value of between about 10% and about 30% of the average peak height is found to give good results. The threshold function comprising the threshold values for all of the segments is then subjected to a least-squares fit to an exponential curve, and the final threshold values for each segment are taken from this curve. The threshold function so produced is often, though not necessarily, a slowly declining exponential.

Steps 200 through 208 are performed for each of four lane signals sA, sT, sG and sC which correspond respectively to lanes containing labelled adenine, thymine, guanine and cytosine, similar to lanes 102, 104, 106, 108 in FIG. 1. When the group of provisional peaks has been selected for each of the four lane signals, a procedure for registering the four lane signals is used. In a preferred embodiment, the peaks are placed not only in correct spatial order across the four lanes, but also are arranged to minimize the variance of their spacing and to center (as nearly as possible) the peaks at the expected locations based on interpeak distances. Preferably, the alignment procedure uses high-speed sorting across the lanes with a four-lane interdependent adjustment of peak positions.

A preferred alignment process for step 210 is described in reference to FIG. 5, and includes a coarse alignment and a fine alignment. A starting alignment is established by assuming that the sample numbers respectively assigned to each of the putative peaks reflects their actual respective relative positions in the set of deconvolved lane signals. A putative interpeak spacing is also determined for the putative peaks, by counting the total number of putative peaks and dividing the total length of the signal by the number of peaks.

Once the starting alignment is performed, coarse alignment proceeds as follows. First, a $4 \times 4$ matrix is set up which contains the average actual interpeak distances of all possible lane-lane combinations organized in row and columns. That is, the interpeak distance for each A-C peak pair in which a peak in the A lane is immediately adjacent to a subsequent peak in the C lane, is recorded in the A-C category, and the values for all such A-C peak pairs are averaged to obtain the A-C matrix element. Similarly, the interpeak distances for all the C-A peak pairs (C lane peak with a subsequent A lane peak) are recorded in the C-A category and averaged to obtain the C-A matrix element. This process is performed for all of the twelve non-identical lane-lane pairs. The row-column combination of every matrix element thus corresponds to a unique lane-lane pair. It does not matter precisely how the rows/columns are specifically ordered. For purposes of describing the alignment process, however, a TCGA $4 \times 4$ matrix as shown in FIG. 5A will be assumed. In the TCGA example, T is the selected reference lane, meaning that the A, G and C lanes will be compared to the T lane and if shifting is necessary, shifted with respect to the T lane.

Next, the transpose of the TCGA four-by-four categorization matrix is computed and added to the original TCGA matrix, and the resulting sum is divided by two. The final $4 \times 4$ matrix values so determined represent independent estimates of the interpeak spacings for each of the individual peak pairs. These matrix-derived spacing values are compared to the putative interpeak spacing (step 506). If a lane is not positioned in the correct order relative to the reference lane, the matrix-derived spacing values for peak pairs of that lane with the reference lane, will differ significantly from the putative peak spacing of step 502. A significant deviation is considered to exist when the absolute difference between the matrix-derived spacing and the putative interpeak spacing is greater than one-fourth of the putative spacing. If the biochemical steps in preparation of the sequence lanes have been very carefully performed, the starting alignment may be satisfactory and the coarse shifting described in the next paragraph may be unnecessary.

To adjust the alignment when one of the lanes is determined to be out of order, an iterative shifting procedure is employed. The incorrectly placed lane is shifted by a delay of one-half of the expected spacing, relative to the reference lane. The spacing matrix values are then recomputed to determine whether a significant deviation from the expected spacing obtained in step 208 still exists. If the spacing values still deviate significantly, the lane is advanced by one-quarter of an expected spacing from the previous shifted position. The iterations of the coarse shifting process are terminated when either a) the difference between the matrix-derived peak-pair spacing and the putative spacing is less than one-fourth of the putative spacing, or b) the absolute difference between the two spacing values is larger for a different one of the non-reference lanes. In the latter case, the shifting process is then performed for the next lane until one of these two criteria is met. Coarse alignment is considered finished when the deviation of spacing values of all the lanes meets criterion a) above.

Once the coarse alignment is deemed satisfactory, or if coarse shifting was not required, a second, fine alignment step is performed. A three-dimensional matrix is established, which has as its first two dimensions the TCGA 4×4 matrix, and a third dimension which is the migration distance (sample number). Each element of the 3D matrix has a pair of values x,y, one specifying the migration distance (sample number) of a given peak-peak occurrence, and the other specifying the interpeak distance for that occurrence. Thus, the fine alignment matrix takes into account the variations in interlane peak spacing with migration distance in the gel.

Next, a spacing vs. distance function (referred to hereinafter as a "spacing function") is derived for each peak pair from the 3D matrix elements, and the functions are fitted to respective straight lines. One lane is selected as the reference lane. Preferably, the reference lane is selected to have the largest interpeak distance of the four lanes, over the entire migration distance (e.g., the largest slope value). The y-intercept of a given lane relative to that of the reference lane, reflects the difference in peak spacing between the non-reference lane and the reference lane at a specific point in the sequence. In the present working embodiment, only three sets of matrix element values are used, which for example when T is the reference lane, would be T-C, T-G and T-A. This is to simplify and speed the computational process. However, if the accuracy obtained is insufficient, additional sets of matrix elements may be included in the fine alignment computations.

The slope of each line represents the actual interpeak spacing as a function of migration distance In the fine alignment process, the slope difference between a reference lane and a second deviating lane, is used to add selected interpolated samples to "stretch" the deviating lane to compensate for the variation in spacing with distance. An interpolated sample is derived by averaging two adjacent samples, and inserting the averaged value as a "virtual" sample midway between the two original samples and spaced from each by the original sample spacing. Thus, interpolation of one sample in effect expands the signal length by one inter-sample distance. The interpolation process thereby compensates for variation in interpeak spacing between peaks in adjacent order within a given lane and/or between two different lanes.

In the current working embodiment, it is assumed that the spacing function is a straight line and thus the shift is also a straight line. However, alternative models may prove to be more accurate, particularly with visualization methods which do not involve direct blotting, such as film exposure directly from a static electrophoresis gel.

Once a satisfactory alignment has been achieved, a peak refinement step 214 is performed. Often, a small percentage of the putative peaks are false peaks. Such false peaks may be produced by background noise, by anomalous background events such as scratches in the surface of the blotting film, and/or by other factors. Most false peaks have a relatively low amplitude, particularly when compared to the "true" peak in one of the other lanes. Therefore, all four normalized aligned lanes are superimposed and only peaks of relatively high amplitude are selected. In this process, most of the false peaks are eliminated.

An average interpeak spacing is then determined as described for alignment step 210. That is, the average interpeak spacing is determined from the total number of samples divided by the number of maximal peaks.

Depending upon the sequence quality, it may be desirable to perform further peak refinement This refinement is intended to detect otherwise unresolved peaks in which the peaks or bands are highly blurred and/or severely overlapped and therefore appear as broad plateaus or shoulders even after the filtering step 204. In the working embodiment, these undetected peaks are resolved by checking the interpeak distances. If the interpeak distance is greater than about 1.7 times the average peak separation, an intermediate peak is added from one of the lanes. Conversely, if the separation between adjacent peaks in the same lane is less than one-half the average interpeak spacing, only the peak with larger amplitude is selected. Thus, certain excess but maximally appearing peaks are also removed by this process. The values 1.7 and 0.5 are empirical. Other values may be used and may prove to give better results.

An alternate technique of peak refinement involves preparing a histogram of the run widths of peaks within a single lane for all of the lanes. This histogram separates the run widths into categories which can be used to determine the number of peaks implied by the run. (A run is considered to be a series of apparent or putative peaks which are adjacent, e.g. correspond to fragments ending in the same nucleotide but differing in length by single nucleotides, in the same lane.) The relationship between the width of a run and the number of peaks in that run is determined by this width histogram. The expected spacing can then be determined from these runs and the width histogram.

Once the peak assignments have been refined and determined to be sufficiently accurate, the sequence of DNA bases is determined. The nucleotide sequence is simply the correspondence between peak order among the different lanes and the lane associated with each peak. This step is referred to as base calling (step 216).

In the working embodiment, the steps of blind deconvolution may be performed either on a computer work station which has been properly programmed or constructed or by a series of signal processing circuits which will be described in greater detail with reference to FIG. 4 hereinafter. Steps 208 through 216, that is, from the preliminary peak detection through base calling to produce the sequence, are performed with a typical computer work station including a microprocessor-based computer having the necessary internal architecture.

However, while the working embodiment employs homomorphic filtering as the step of blind deconvolution, other methods of blind deconvolution are known and may also provide adequate results. It is also within contemplation that other types of lifter functions, other values of the lifter function shown in FIGS. 8-9, and/or other types of noise filters for step 312, may provide satisfactory results while not departing from the general concept and spirit of the invention.

Additionally, principle features of the alignment process described in reference to FIG. 5, including coarse alignment using a 4×4 matrix, coarse lane shifting, fine alignment with the 3D matrix, and interpolation of samples, may be applied to a signal set representing an entire DNA sequencing gel, or on a segment-by-segment basis to sub-segments within the gel.

In the latter case, the segments must then be properly aligned with respect to each other. This can be done with essentially the same alignment methods as for the case of aligning multiple lanes, except that overlapping portions of adjacent sequence segments are being used. The alignment process may also be used to align sequences from different sequencing gels provided that there is a suitable overlap between the two sequences. Such alignment of overlapping adjacent sequences desirably is performed with a technique termed herein "overlap-add".

Figure 4A:
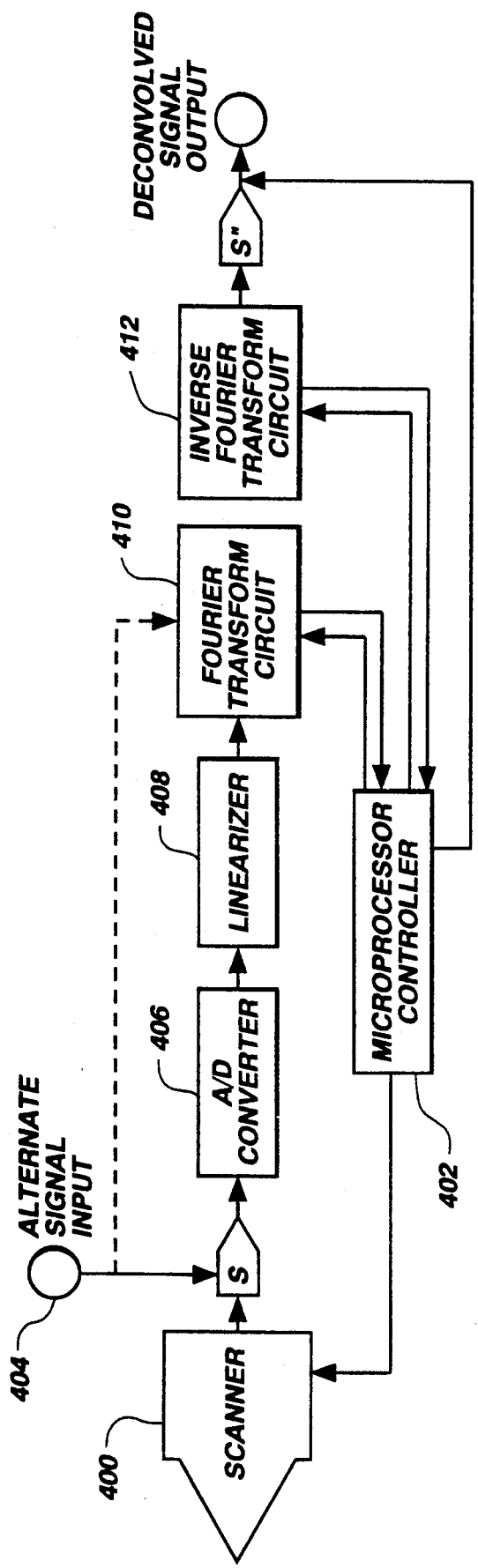
FIG. 4A is a block diagram of an apparatus for performing the peak sharpening method of FIG. 3.
Figure 4B:
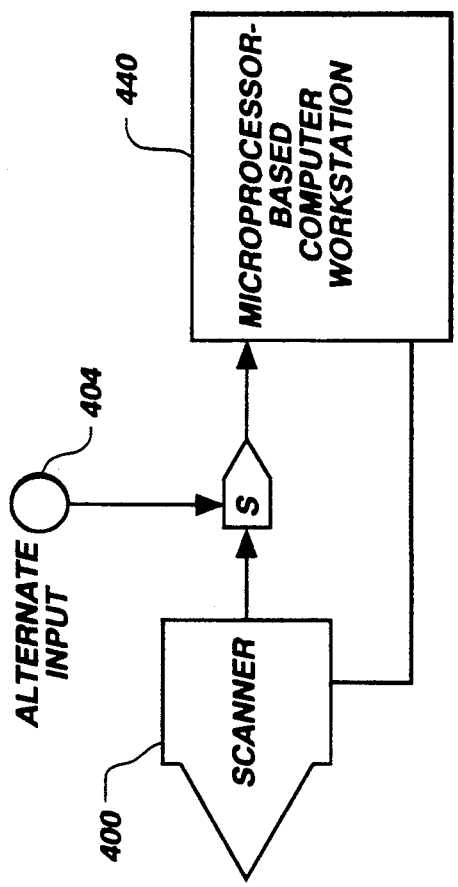
FIG. 4B is a block diagram of an alternate embodiment of an apparatus for performing the invention.

FIGS. 4A and 4B depict apparatus which are capable of carrying out the peak sharpening process of the invention. The apparatus of FIG. 4A includes a scanner 400 for scanning autoradiographs, which outputs a scan signal. Scanner 400 is connected to be controlled by a microprocessor controller 402 which includes a ROM or other essentially permanent memory unit containing certain look-up tables for performing complex logarithm and complex exponential conversions. Because both conversions involve complex signals, two look-up tables each operating in two dimensions are required for each of the noted conversions, one for the real signal portion and one for the imaginary signal portion.

Desirably, the apparatus also includes an alternate signal input 404 through which data signals from a free-standing scanner or other detector type (such as radiation detector or photon detector other than a photographic film) can be input to the apparatus. Optionally, the apparatus may include an A/D converter 406 for converting either scan signals or other data signals from analog to digital form. Further optionally but highly desirably, the apparatus may include a linearizer 408 for linearizing signals S which are received in a non-linear form. Linearizer 408 is connected to send the linearized signal to FT (Fourier transform) circuit 410 to undergo the Fourier transformation of step 300.

Alternatively, linearizer 408 may be embodied as a look-up table stored in the permanent memory of controller 402. In the latter embodiment, A/D converter 406 would be connected to send its output to controller 402 which in turn would send the linearized signal to FT circuit 410.

FT circuit 410 is connected to receive a linearized signal either from linearizer 408 or from microprocessor 402, depending upon the specific embodiment. Both FT circuit 410 and inverse FT circuit 412 are connected for two-way communication with controller 402, and are operable respectively to perform Fourier transformations and inverse Fourier transformations on received signals.

Controller 402 is operable via instructions stored in permanent memory storage to perform the following steps: read an FS signal resulting from Fourier transformation of the linearized signal; convert the FS signal to a log-spectrum signal using the appropriate look-up tables enumerated previously herein; send the real portion of the log-spectrum signal to inverse FT circuit 412 and retain the imaginary portion in temporary memory until it is needed; read a cepstrum signal output by inverse FT circuit 412 in response thereto; multiply the cepstrum signal by a lifter function stored in permanent memory; send the liftered cepstrum signal to FT circuit 410; read the liftered log-spectrum signal output by FT circuit 410 in response thereto; add back the imaginary portion of the original log-spectrum signal; convert the resulting liftered CLS signal to its antilog, e.g. to a liftered FS signal, using the appropriate look-up tables; apply a low-pass noise filter to liftered FS signal; and send the noise-filtered liftered FS signal to inverse FT circuit 412 to generate the final deconvolved signal. The deconvolved signal is then outputted by inverse FT circuit 412.

FT circuit 410 and inverse FT circuit 412 may be embodied as commercially available analog or digital logic circuits. Preferably, circuits 410, 412 are digital chips which employ FFT (fast Fourier transform) technology. Chips which can be used for FFT computation in the role of circuits 410, 412 include so-called DSP (digital signal processing) chips such as the TMS 320C10, 320C25, 320C15, and 320C30 available from Texas Instruments. Similar chips are available from other sources.

FIG. 4B depicts an alternate embodiment of an apparatus for performing the peak sharpening method. In this embodiment, all of the components of the embodiment of FIG. 4A except for scanner 400 and outside signal input 404 are replaced by a microprocessor-based computer workstation 440. Workstation 440 is configured to perform all of the functions of controller 402 and, additionally, to perform Fourier transformations and inverse Fourier transformations using signal processing logic means. Workstation 440 may either be programmed with the necessary look-up tables or may have means such as a disk reader for reading the tables when appropriate.

The apparatus of FIG. 4B may desirably be additionally configured to perform the methods of DNA sequence analysis outlined in steps 208-216 of FIG. 2 and in FIG. 5.

Preferably, in the embodiment of FIG. 4B, the digital logic processing means encompassed in computer workstation 440, uses the well known Cooley-Tukey Fast Fourier Transform (FFT) algorithm, to provide the fastest signal processing consistent with modern signal processing technology.

Still another embodiment of an apparatus includes a free-standing deconvolver comprising at least elements 402, 404, 410, and 412 of FIG. 4A (and optionally any or all of scanner 400, A/D converter 406, and linearizer 408), plus a computer workstation 440 configured to perform the steps of the method depicted in FIG. 5, as well as steps 208-216 of FIG. 2.

FIGS. 6-12 depict various stages of the homomorphic filtering process of FIG. 3. Except where indicated, the sample numbers indicated on the X axis refer to the same 300 sample segment within a larger 2048 sample block which represents half of a complete gel scan. In all of FIGS. 6-12, sample numbers refer to the position within the entire scan rather than within the 2048 sample block. Also shown in FIGS. 6 and 12 is the correct sequence for the plotted data, as A, T, G, or C indicated along the upper edge of the chart.

Figure 8:
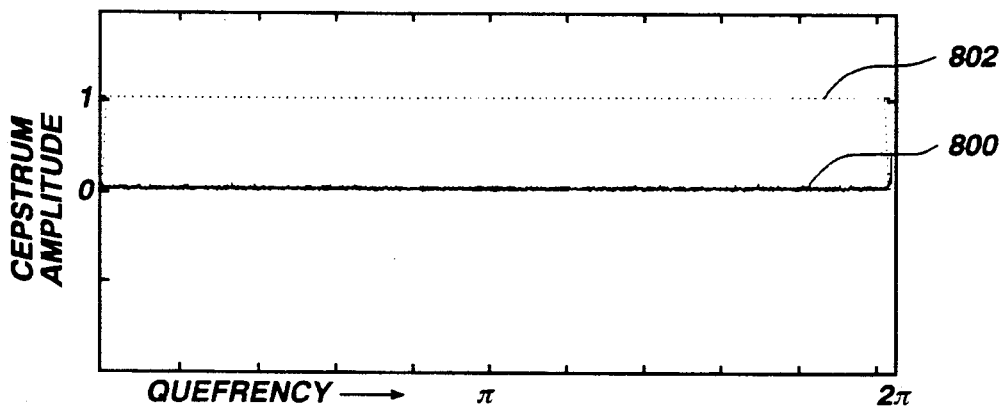
Figure 9:
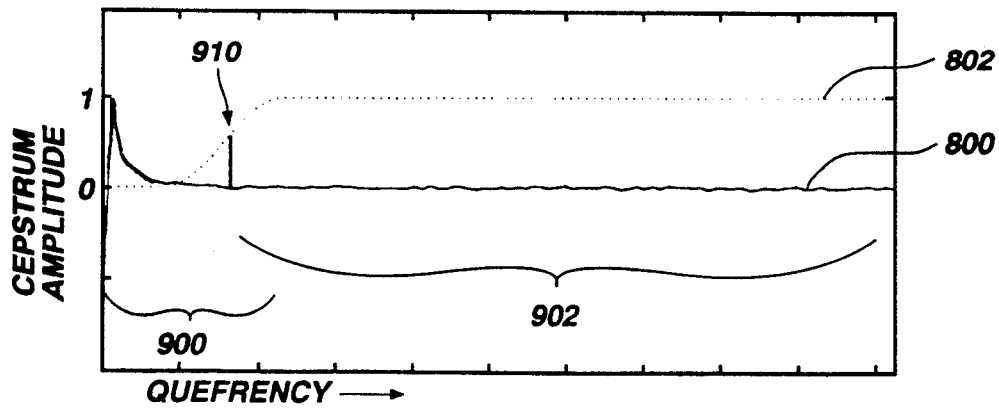

FIG. 6 depicts the lane signals 602, 604, 606 and 608 following linearization. FIGS. 7-11 are charts depicting the results of processing of lane signal 602 at various subsequent stages of the homomorphic filtering of FIG. 3. The abscissae of FIGS. 7, 10A, 10B, 11A and 11B are frequency units scaled between 0 and $2\pi$, or for smaller segments of approximately $0.29\pi$ (FIGS. 10B, 11B). The abscissae of FIGS. 8 and 9 are frequency units (frequency in the cepstral domain). FIG. 12 depicts a set of four deconvolved signal segments, derived from the lane signal segments of FIG. 6 by the method of FIG. 3, including that derived from lane signal 602.

Figure 7:
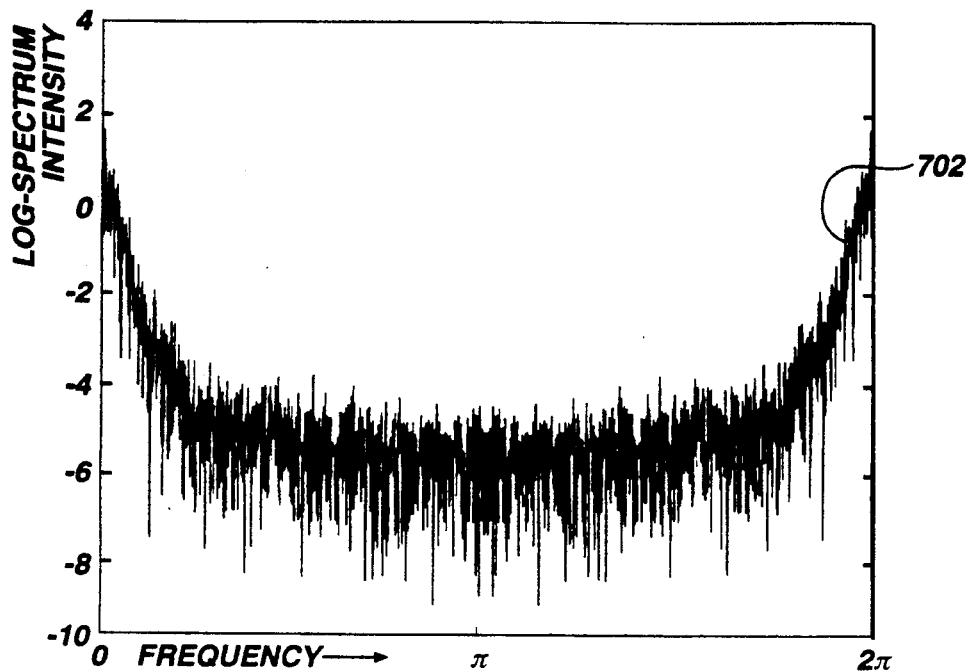
FIGS. 7-11 are charts illustrating the results at various steps in the method of FIG. 3 as applied to one of the lane signals of FIG. 6.

FIG. 7 depicts an LS (log-spectrum) signal 700 produced by step 302. FIG. 8 depicts a cepstrum signal 800 produced in step 304, overlaid with the lifter function 802 which is applied in step 306. FIG. 9 is a higher resolution view of the cepstrum signal 800 and the lifter function 802 in a 300-sample region near the origin. The region in which the blurring function makes its major contribution is a low-frequency region 900, and the lifter function 802 is accordingly designed to reduce and/or eliminate signal components in region 900 while leaving most of the desired signal portion 902 unaffected.

Figure 10A:
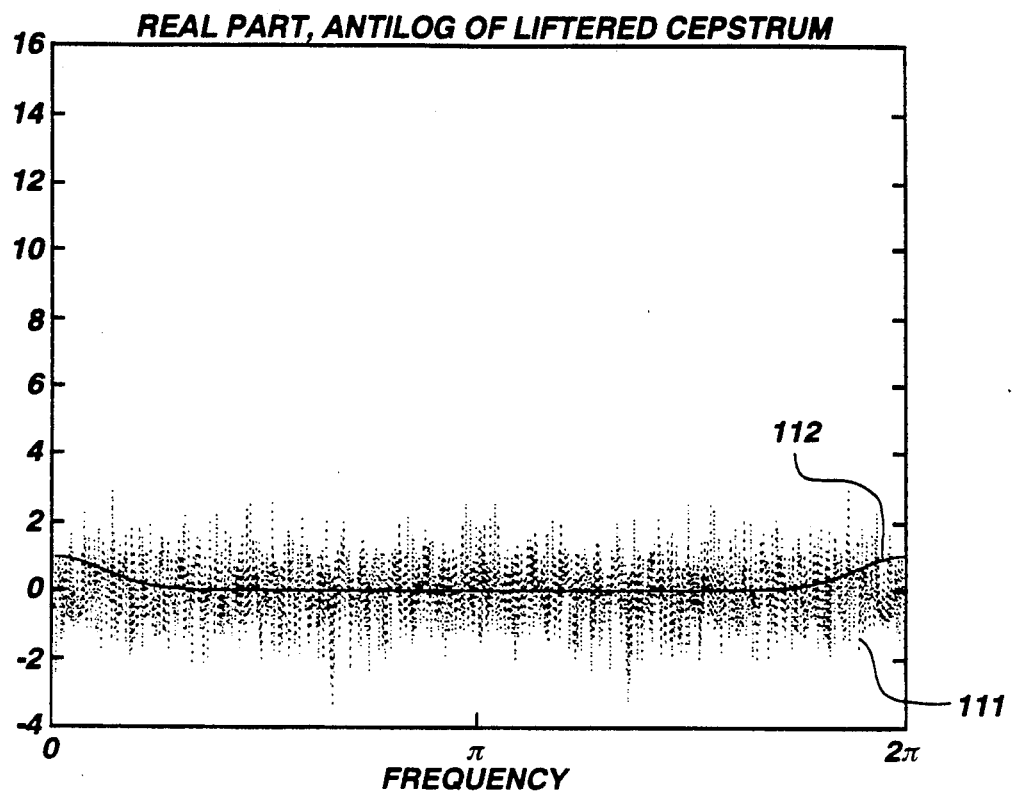
Figure 10B:
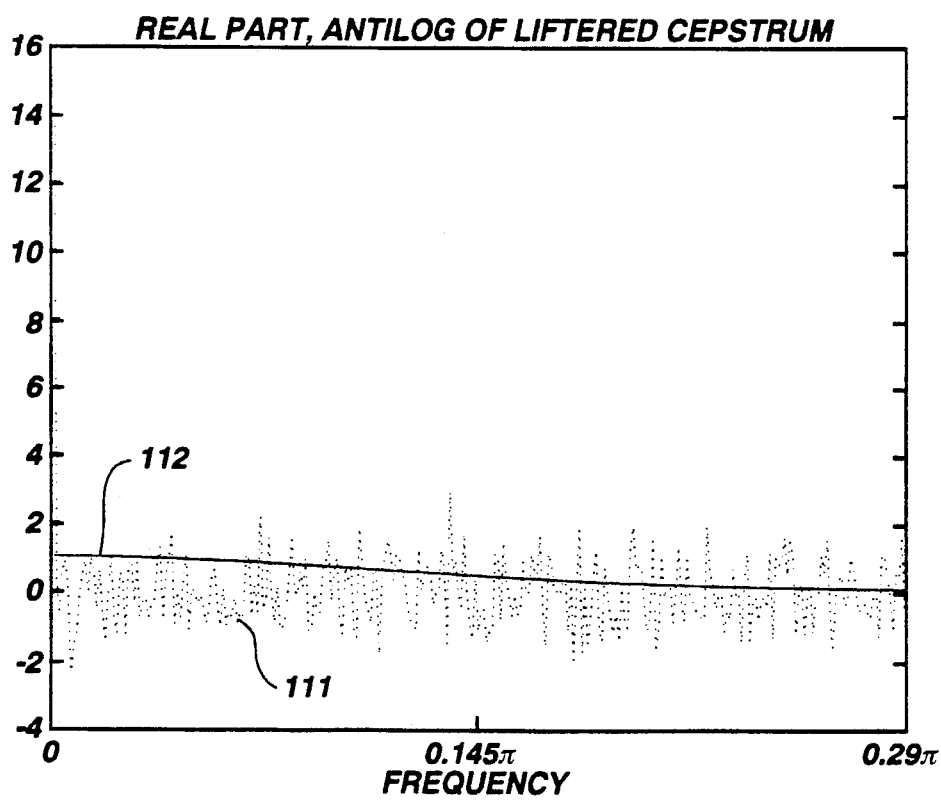

FIG. 10A depicts the real part of the antilog of the liftered cepstrum, e.g. the liftered FS signal resulting from step 310 (dotted line 111), overlaid with the Gaussian noise filter (solid line 112). FIG. 10B is a higher resolution view of the liftered FS signal 111 and the noise filter 112 in a region near the origin.

Figure 11A:
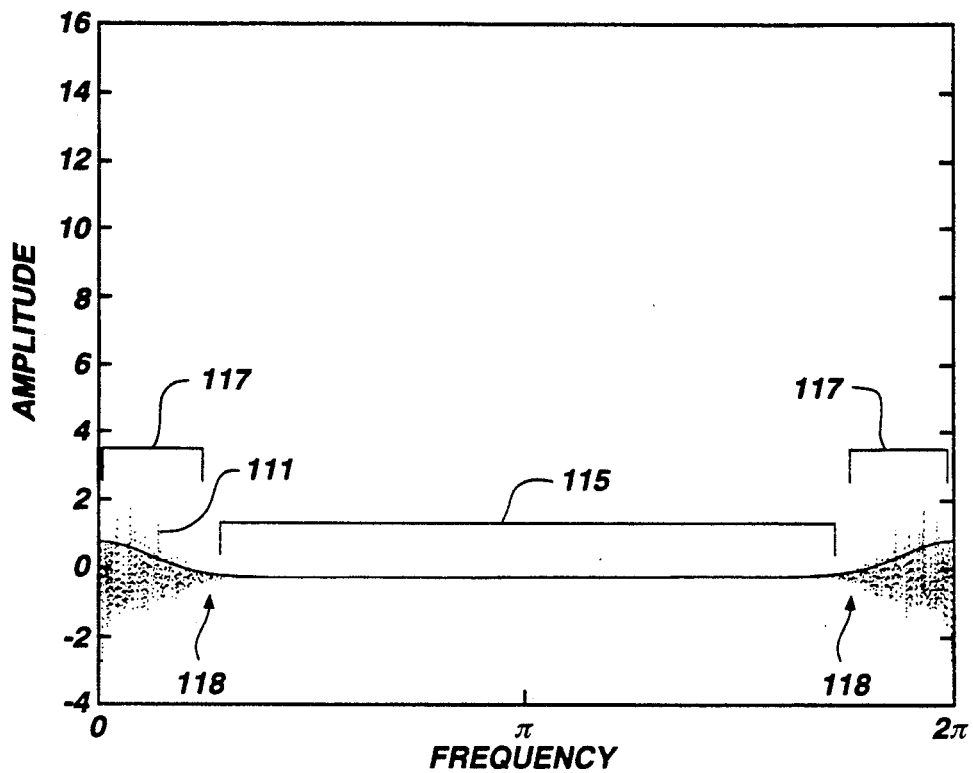
Figure 11B:
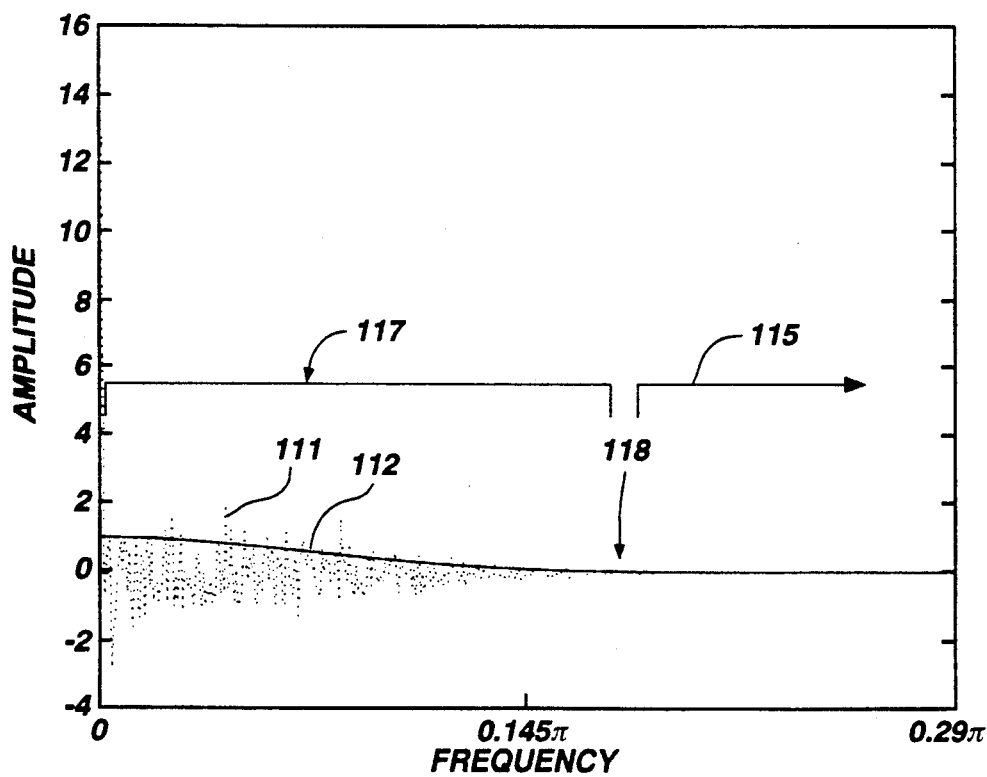

FIG. 11A depicts the result of step 312 of filtering the liftered FS with the noise filter 112, that is the filtered LFS signal 114 (dotted line). Lowpass filter function 112 is overlaid on the filtered LFS. FIG. 11B is an enlarged view of a 300-sample portion of FIG. 11A. Region 115 approximates the frequency region where noise makes a substantial contribution to the signal, and accordingly the noise filter function 112 is shaped to reduce and/or eliminate much of the signal in region 115 while leaving a desired signal region 117 largely intact.

Finally, FIG. 12 depicts a set of four deconvolved lane signals 122, 124, 126, 128 which respectively result at step 314 for each of the four original lane signals 602, 604, 606, 608, after alignment as in step 210 of FIG. 2.

It should be noted that proteins and protein fragments may also be analyzed by electrophoretic methods, and that such analysis will similarly produce lanes, which may be represented by digital or analog lane signals produced by a scanner or other detector. The analytical method for sharpening peaks which is discussed with reference to FIG. 3 is also suitable for application to autoradiograms representative of proteins and protein fragments, using essentially the same low-pass noise filter.

Furthermore, the method and apparatus may also be useful to sharpen peaks and remove background noise from signals representing chromatographic data such as HPLC (high-pressure liquid chromatography), TLC (thin-layer chromatography), etc. Some modification of the precise values of the lifter function and/or the noise filter may be necessary to accommodate differences in the chromatographic method and/or the technique (e.g. absorption measurement, fluorescent emission, etc) by which the data are obtained. Such modifications will be apparent to those skilled in the art, when they are familiar with the teachings of this application.

A significant advantage of the blind deconvolution is that a single homomorphic filtering function ("lifter") with an appropriately chosen set of numerical values, can be used to deconvolve all linearized lane signals derived by a given chromatographic technique (understood in this context to include the method by which the component distribution or migration pattern is visualized). This is essentially true regardless of variations in relative signal intensity and/or background noise among different signals obtained by the same technique.

When the method of blind deconvolution or homomorphic filtering is applied to an autoradiogram representative of protein fragments, some of the steps of the complete method for DNA sequence analysis depicted in the flow chart of FIG. 2 will vary, as proteins analyzed by gel electrophoresis will not necessarily generate a sequence of fragments whose spacing is expected to correspond to a known approximate increment of migration distance, as is the case in DNA sequencing samples. Although proteins and protein fragments may not possess the periodic nature characteristic of DNA sequencing samples, Fourier analysis is nevertheless capable of producing functions which represent otherwise apparently random peak distributions, and therefore is entirely applicable to autoradiograms representing proteins or protein fragment migration, as well as to other types of chromatograms.

What is claimed is:

1. A method of sharpening peaks in a signal representing a chromatographic distribution of components from a biochemical mixture separated by a chromatographic method comprising the steps of:
   providing a signal representing a chromatographic distribution of components from a biochemical mixture separated by a chromatographic method;
   transforming the signal from its original space domain to a cepstrum;
   manipulating the cepstrum with a lifter function selected to substantially reduce the amplitude of a portion of the cepstrum which is attributable to a blurring function, thereby producing a liftered cepstrum signal; and
   de-transforming the liftered cepstrum signal to produce a deconvolved lane signal in the original space domain.

2. The method of claim 1, further including a step of noise filtering for substantially removing the effects of background noise in the deconvolved lane signal.

3. The method of claim 2, wherein said step of noise filtering is performed in conjunction with said step of de-transforming.

4. The method of claim 3, wherein said step of noise filtering comprises applying a Gaussian lowpass filter having a bandwidth of between about 0.024A and about 0.072A, where A = the number of samples comprising $\pi$.

5. The method of claim 2, wherein in said step of manipulating the cepstrum, the cepstrum is multiplied by the lifter function and the lifter function is configured to have a first portion which attenuates the cepstrum in a low-frequency region of the cepstrum and a second portion which is substantially equal to one in a high-quefrency region of the cepstrum.

6. The method of claim 5, wherein the first portion of the lifter function has the approximate shape of a 50% cosine taper which reaches an ordinate value of 0.50 at a selected point between the low-quefrency region and the high-quefrency region of the cepstrum.

7. The method of claim 6, wherein said selected point is located approximately in the region in which the value of the cepstrum reaches a plateau.

8. A method of sharpening peaks in a signal representing a chromatographic distribution of components from a biochemical mixture separated by a chromatographic method comprising the steps of:

provoking a signal representing a chromatographic distribution of components from a biochemical mixture separated by a chromatographic method;

generating an FS (frequency spectrum) signal by Fourier transformation of the signal;

taking the log of the FS signal to produce a CLS (complex log-spectrum) signal;

taking an inverse Fourier transform of the real portion of the CLS signal to produce a cepstrum signal;

multiplying the cepstrum signal by a lifter function chosen to reduce the contribution of a blurring function, thereby producing a liftered cepstrum signal;

subjecting the liftered cepstrum signal to Fourier transformation to produce an LLS (liftered log-spectrum) signal;

adding the imaginary portion of the LS signal to the LLS signal to produce a liftered CLS signal;

taking the inverse logarithm of the liftered CLS signal to produce a liftered FS (liftered frequency spectrum) signal; and taking the inverse Fourier transform of the liftered FS signal to produce a deconvolved signal.

9. The method of claim 8, further including a step of removing noise from the signal being processed, said step of removing noise being performed after said step of producing an FS signal.

10. The method of claim 9, wherein said step of removing noise is performed upon said liftered FS signal before said step of taking the inverse Fourier transform, and comprises applying a low-pass filter to said liftered FS signal, to substantially remove frequencies above a selected cut-off frequency and produce a noise-filtered FS signal.

11. The method of claim 10, wherein said low-pass filter is a Gaussian filter having a bandwidth equivalent to between about 50 and 150 frequency samples when $\pi$ is 1024 samples.

12. The method of claim 9, wherein the lifter function is a high-pass type having a first portion which attenuates the cepstrum in a low-frequency region of the cepstrum and a second portion which is substantially constant through a high-frequency region of the cepstrum.

13. The method of claim 12 wherein the second portion of the lifter function is selected to normalize the amplitude of the cepstrum to a chosen range.

14. The method of claim 13, wherein the first portion of the lifter function approximately conforms to a 50% cosine taper which reaches an ordinate value of 0.50 at a selected point between the low-frequency region and the high-frequency region of the cepstrum.

15. The method of claim 13, wherein said selected point is located approximately in the region in which the value of the cepstrum reaches a plateau.

16. The method of claim 9, wherein the biochemical mixture is selected from the group consisting of: mixtures of polypeptides, sets of DNA fragments generated in a DNA sequencing reaction, mixtures of organic chemicals, and mixtures of fluorescently labelled cells or subcellular components including organelles, nuclei, chromosomes, and fragments thereof.

17. The method of claim 16, wherein the chromatographic method is selected from the group consisting of: electrophoresis, high-pressure liquid chromatography, fluorescence-activated separation, affinity chromatography, thin-layer chromatography, paper chromatography.

18. A method of determining a nucleotide sequence of a DNA molecule from an electrophoretic migration pattern of a set of DNA sequencing lanes sufficient to establish the relative migration patterns of fragment groups respectively terminating in each one of the nucleotides designated A, T, G and C, comprising the steps of:

providing a set of lane signals respectively encoding the migration patterns of each member of the set of sequencing lanes, and each lane signal having peaks representing the relative amounts of DNA fragments of different sizes present in the corresponding lane;

identifying putative peaks in all of the lane signals and determining a putative spacing which is the average for all of the putative peaks;

aligning the lane signals to establish a provisional ordering of the putative peaks;

generating a three-dimensional matrix having a plurality of matrix elements, each matrix element taking the form of a coordinate pair comprising a spacing value for a specific occurrence of a peak pair, and the location in the signal of that specific occurrence, wherein a peak pair is defined as a pair of non-identical peaks which are adjacent each other in the provisional ordering;

deriving a peak pair spacing function for each category of peak pair;

selecting a reference lane; and adjusting the number of samples within each lane signal as needed to produce a spacing function for the lane signal which substantially matches the spacing function of the reference lane, thereby producing a set of fully aligned lane signals; and reading a DNA sequence from the order of peaks in the aligned lane signals 19. The method of claim 18, further including a step of fitting the peak pair spacing function to a straight line, performed prior to said step of selecting a reference lane.

20. The method of claim 18, wherein said step of identifying putative peaks comprises the steps of establishing a threshold function and selecting peaks whose intensity exceeds the value of the threshold function.

21. The method of claim 20, wherein the threshold function is a variable threshold function selected to reflect the variation in average peak intensity with position in the signal.

22. The method of claim 21, further including a step of coarse alignment of the lane signals, said step of coarse alignment being performed after said step of identifying putative peaks and before said step of generating a three dimensional matrix.

23. The method of claim 22, wherein said step of coarse alignment includes the following substeps:

deriving a plurality of peak pair spacings, one corresponding to each possible non-identical peak pair;

comparing each of the peak pair spacings to the putative spacing;

selecting a coarse reference lane; and shifting by a selected increment relative to the coarse reference lane, each non-reference lane for which the absolute value of the difference between its individual peak pair spacing and the putative spacing differs by a significant amount from the value for the coarse reference lane.

24. The method of claim 23, wherein after said step of shifting by an increment, the following further steps are performed, comprising:

re-computing the peak pair spacing for the shifted lanes to produce a corresponding number of adjusted peak pair spacings and comparing the absolute difference value for each shifted lane to that of the coarse reference lane; and interatively repeating said steps of shifting lanes, re-computing the peak pair spacing, and comparing the absolute difference values until a satisfactory coarse alignment is achieved.

25. The method of claim 18, further including a step of blind deconvolution of said lane signals performed prior to said step of identifying putative peaks.

26. The method of claim 25, wherein said step of blind deconvolution comprises the following steps:

transforming the signal from its original space domain to a cepstrum;

manipulating the cepstrum with a lifter function selected to substantially reduce the amplitude of a portion of the cepstrum which is attributable to a blurring function, thereby producing a liftered cepstrum signal; and de-transforming the liftered cepstrum signal to produce a deconvolved lane signal in the original space domain.

27. The method of claim 26, further including a step of noise filtering performed in conjunction with said step of de-transforming to produce a noise-filtered deconvolved signal.

28. The method of claim 27, wherein in said step of manipulating the cepstrum, the cepstrum is multiplied by the lifter function and the lifter function is configured to have a first portion which attenuates the cepstrum in a low-frequency region of the cepstrum and a second portion which is substantially equal to one in a high-frequency region of the cepstrum.

29. A method of aligning the members of a set of lanes of a DNA sequencing electrophorogram, comprising the steps of:

providing a set of lane signals respectively encoding the migration patterns of each member of the set of sequencing lanes, and each lane signal having peaks representing the relative amounts of DNA fragments of different sizes present in the corresponding lane;

establishing a provisional alignment of the lanes;

generating a three-dimensional matrix having matrix elements in the form of coordinate pairs, each coordinate pair comprising a peak pair spacing value for an individual occurrence of that peak pair, and the signal position of the individual occurrence;

deriving a peak pair spacing function for each category of peak pair, and fitting the spacing function to a straight line;

selecting a reference lane; and adjusting the number of samples within each lane signal as needed to produce a spacing function for the lane signal which substantially matches the spacing function of the reference lane.

30. The method of claim 29, wherein said step of selecting a reference lane is performed by selecting the lane whose spacing function has the largest slope value when compared with the spacing functions of the other members of the set.

31. The method of claim 30, wherein said step of establishing a provisional alignment comprises the steps of:

aligning the lane signals to establish a provisional ordering of the putative peaks;

deriving a plurality of peak pair spacings, one corresponding to each possible non-identical peak pair;

comparing each of the peak pair spacings to the putative spacing;

selecting a coarse reference lane;

shifting by a selected increment relative to the coarse reference lane, each non-reference lane for which the absolute value of the difference between its individual peak pair spacing and the putative spacing differs by a significant amount from the value for the coarse reference lane;

re-computing the peak pair spacing for the shifted lanes to produce a corresponding number of adjusted peak pair spacings and comparing the absolute difference value for each shifted lane to that of the coarse reference lane; and interatively repeating said steps of shifting lanes, re-computing the peak pair spacing, and comparing the absolute difference values until a satisfactory coarse alignment is achieved.

32. The method of claim 30, wherein said step of establishing a provisional alignment includes the steps of:

identifying putative peaks by determining a variable threshold function based on the variation in average peak intensity with position in the signal; and selecting peaks whose intensity exceeds the value of the threshold function.

33. A method of determining a DNA sequence from an electrophorogram of a set of nucleic acid sequencing lanes, comprising the steps of:

providing a set of lane signals, each representing a corresponding one of a set of sequencing lanes and comprising a peak signal function convolved with a blurring function, the peak signal function comprising peaks reflective of the relative amounts of particular fragments in the sequencing lane;

processing by blind deconvolution each of said lane signals to reduce the contribution of the blurring function to each lane signal, thereby producing a set of corresponding deconvolved lane signals;

mutually aligning said lane signals to establish an ordering of peaks among the respective lanes; and reading a nucleic acid sequence from the order of peaks in the aligned lane signals.

* * * * *